(12) United States Patent
Amador et al.

(10) Patent No.: US 7,516,417 B2
(45) Date of Patent: Apr. 7, 2009

(54) DISPLAY PARAMETER ADJUSTMENT

(75) Inventors: Rich Amador, Fullerton, CA (US); Richard R. Neugebauer, Huntington Beach, CA (US)

(73) Assignee: Canon U.S.A., Lake Success, NY (US)

( * ) Notice: Subject to any disclaimer, the term of this patent is extended or adjusted under 35 U.S.C. 154(b) by 446 days.

(21) Appl. No.: 11/000,151

(22) Filed: Nov. 29, 2004

(65) Prior Publication Data
US 2006/0117270 A1 Jun. 1, 2006

(51) Int. Cl.
*G06F 3/00* (2006.01)
*G09G 5/00* (2006.01)
*G09G 5/02* (2006.01)

(52) U.S. Cl. .................. 715/788; 715/722; 345/617; 345/594

(58) Field of Classification Search .................. 715/722; 345/617, 594
See application file for complete search history.

(56) References Cited

U.S. PATENT DOCUMENTS

| | | | | |
|---|---|---|---|---|
| 5,270,530 | A * | 12/1993 | Godlewski et al. | 250/208.1 |
| 5,447,153 | A * | 9/1995 | Weil et al. | 600/300 |
| 5,539,426 | A * | 7/1996 | Nishikawa et al. | 345/635 |
| 5,898,436 | A | 4/1999 | Stewart et al. | 345/354 |
| 5,930,009 | A | 7/1999 | Sato et al. | 358/518 |
| 6,181,321 | B1 | 1/2001 | Zhao et al. | 345/150 |
| 6,400,377 | B1 * | 6/2002 | Hiraka et al. | 715/716 |
| 6,461,298 | B1 * | 10/2002 | Fenster et al. | 600/437 |
| 2002/0126302 | A1 | 9/2002 | Fukao | 358/1.9 |
| 2003/0194117 | A1 * | 10/2003 | Okuzawa | 382/128 |
| 2004/0051710 | A1 * | 3/2004 | Hara | 345/419 |
| 2004/0057061 | A1 | 3/2004 | Bochkarev | 358/1.9 |
| 2004/0057614 | A1 | 3/2004 | Ogatsu et al. | 382/162 |
| 2005/0197567 | A1 * | 9/2005 | Qian et al. | 600/425 |
| 2006/0056680 | A1 * | 3/2006 | Stutsman et al. | 382/154 |
| 2006/0093207 | A1 * | 5/2006 | Reicher et al. | 382/156 |

OTHER PUBLICATIONS

Terry Yoo and Penny Rheingans Digital design of a surgical simulator for interventional MR imaging Copyright 1999 IEEE pp. 393-396A.*
Ulead PhotoImpact 3.0 User Guide Jan. 1996 pp. 99-100.*
PhotoImpact 10 User Guide Ulead Systems, Inc Aug. 2004 pp. 49 and 93.*

* cited by examiner

*Primary Examiner*—Doug Hutton
*Assistant Examiner*—Andrea N Long
(74) *Attorney, Agent, or Firm*—Fitzpatrick, Cella, Harper & Scinto

(57) ABSTRACT

A user interface for the adjustment of display parameters. The user interface includes a plurality of selectable icons arranged in a matrix, each icon having a visual cue indicating the display adjustment achieved by the selection of the icon. The visual cues may include level and window number values and grayscale patches. The level and window number values are calculated from a default center value obtained from a digital image file to be displayed and a predetermined gradient.

17 Claims, 6 Drawing Sheets

DISPLAY PARAMETER ADJUSTMENT

BACKGROUND AND SUMMARY

1. Field of the Invention

The present invention generally relates to the adjustment of display parameters, and more specifically to a user interface for the adjustment of display parameters.

2. Description of the Related Art

Manufacturers of display devices generally support user controls for the adjustment of display parameters. For example, conventional display devices often have a manual user interface for adjusting the brightness and contrast of the display. In addition, many software image editors include user interfaces for altering display parameters, such as hue, chroma and saturation.

Typically, such user interfaces are arranged with controls that adjust one parameter at a time. For example, typical display adjustment user interfaces may include increment/decrement buttons or slider bars. Adjustment of display parameters with such interfaces often require multiple user interactions (e.g. multiple mouse clicks) as most users will adjust multiple parameters on the display device. In addition, such user interfaces do not provide an indication to the user as to what effect each change of a display parameter will have on the display. As such, display adjustment often becomes a case of trial and error, and can become cumbersome and inefficient.

In particular, adjustment of display parameters for digital radiographic images can become difficult, as both level and window settings may be required to be adjusted. Window and level are terms used in digital radiography to define the range and center of range of grayscale pixels displayed in an image. Window and level are sometimes used synonymously with contrast and brightness. Since conventional display adjustment user interfaces require that the level and window settings be adjusted independently, the number of adjustment iterations can become numerous. Attempts have been made to create and store explicit window and level settings that may be selected from a menu. However, these settings are typically arbitrarily assigned, and do not provide an indication to the user as to the effect the selected values will have on the display.

In view of the difficulty of using conventional user interfaces for adjustment of display parameters, it is desirable to have a more efficient and intuitive user interface.

SUMMARY OF THE INVENTION

In view of this problem, the present invention provides a display adjustment apparatus for adjusting image display parameters. The display adjustment apparatus has a plurality of selectable icons, each icon being associated with a plurality of image display parameters, and a display processing unit for adjusting the display in accordance with the plurality of image display parameters associated with the selected icon.

In accordance with one aspect of the present invention, the selectable icons include a visual cue of a window display setting and a level display setting achieved by selection of an icon.

In accordance with another aspect of the invention, the visual cue includes a level number, a window number, a level grayscale patch which indicates a relative level display setting, and a window grayscale patch which indicates a relative window display setting.

In accordance with still another aspect of the present invention, the plurality of selectable icons are arranged in a matrix.

In accordance with another aspect of the invention, the display adjustment apparatus further includes a calculation unit for calculating the level number and the window number for each of the plurality of selectable icons, and for generating the level grayscale patch and window grayscale patch for each of the selectable icons. The level number and window number are calculated using a function of a center level value, a center window value, and a gradient. The center level value and center window value may be directly obtained from a digital image file to be displayed on the display.

In accordance with another aspect of the invention, the display adjustment apparatus further includes a selectable level reset icon, a selectable window reset icon, and a selectable window/level reset icon. The apparatus also includes a level recalculation unit for recalculating the level number for each of the selectable icons in response to a selection of the level reset icon, wherein a currently selected level number is assigned as the center level value, and the remaining level values are recalculated with a function of the assigned center level value and the gradient. The apparatus further includes a window recalculation unit for recalculating the window number for each of the selectable icons in response to a selection of the window reset icon, wherein a currently selected window number is assigned as the center window value, and the remaining window values are recalculated with a function of the assigned center window value and the gradient. The apparatus further includes, a window/level reset unit for resetting the window and level values to default values.

In accordance with another aspect of the invention, there is provided a display adjustment method for adjusting image display parameters of a display. The method includes the steps of generating a plurality of visual cues, each visual cue being associated with a plurality of image display parameters, displaying the visual cues on a plurality of selectable icons, receiving a selection of one of the selectable icons, and adjusting the display in accordance with the image display parameters associated with the visual cue of the selected icon.

This brief summary has been provided so that the nature of the invention may be understood quickly. A more complete understanding of the invention can be obtained by reference to the following detailed description of the preferred embodiment thereof in connection with the attached drawings.

DETAILED DESCRIPTION

The present invention provides a user interface for the adjustment of display parameters in a computing environment. The user interface consists of a plurality of selectable icons, which may be implemented as selectable buttons within an operating system or computer program of a computing device. The buttons may be selected by a mouse, or by a stylus in conjunction with a touch screen. In addition, the selectable icons may be implemented as mechanically activated switches. For example, the selectable icons may be implemented as push buttons on a monitor.

Selection of one of the icons causes the computing device to adjust a plurality of display parameters. Examples of display parameters that may be adjusted include brightness, contrast, color, hue, and chroma. Such adjustment may affect an entire display device, such as the settings for an LCD monitor. In addition, the display adjustment may only affect one portion of a computer program window. For example, adjustment may be limited to the image viewing portion of a photo editor program.

The selectable icons of the invention's user interface are adapted to adjust a plurality of display parameters with the selection of one icon. For example, the icons may be adapted to adjust both contrast and brightness settings in accordance with predetermined brightness and contrast values associated with the button. To aid the user in the selection of an appropriate display setting, the selectable icons include a visual cue which indicates to the user the effect of the selection of a button.

In this way, the invention provides a display adjustment apparatus for adjusting image display parameters. The apparatus includes a plurality of selectable icons, each icon being associated with a plurality of image display parameters, and a display processing unit for adjusting the display in accordance with the plurality of image display parameters associated with the selected icon.

Figure 1:
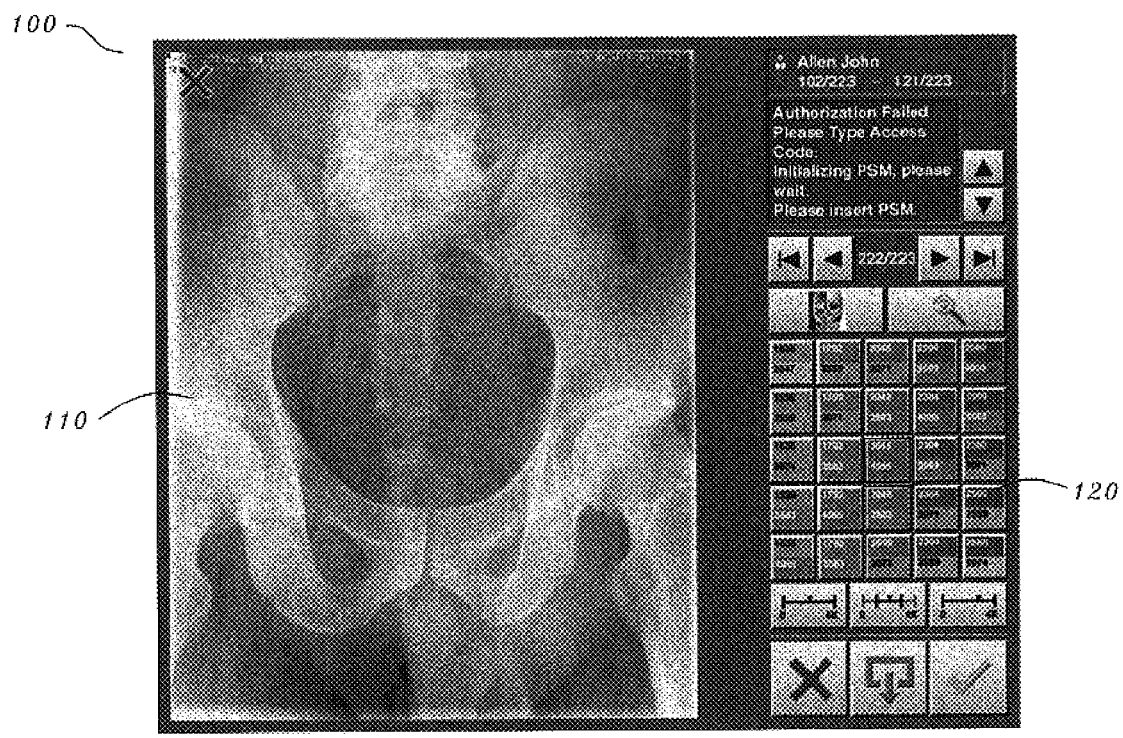
FIG. 1 is a representation of a computing environment for the user interface of the invention.

FIG. 1 depicts one embodiment of a display adjustment user interface according to the invention. Display adjustment user interface 120 may be utilized within program window 100 of a computer program capable of viewing digital images. For example, the computer program may be a program for viewing digital radiographic images, such as X-rays. The images are displayed in image window 110.

Figure 2A:
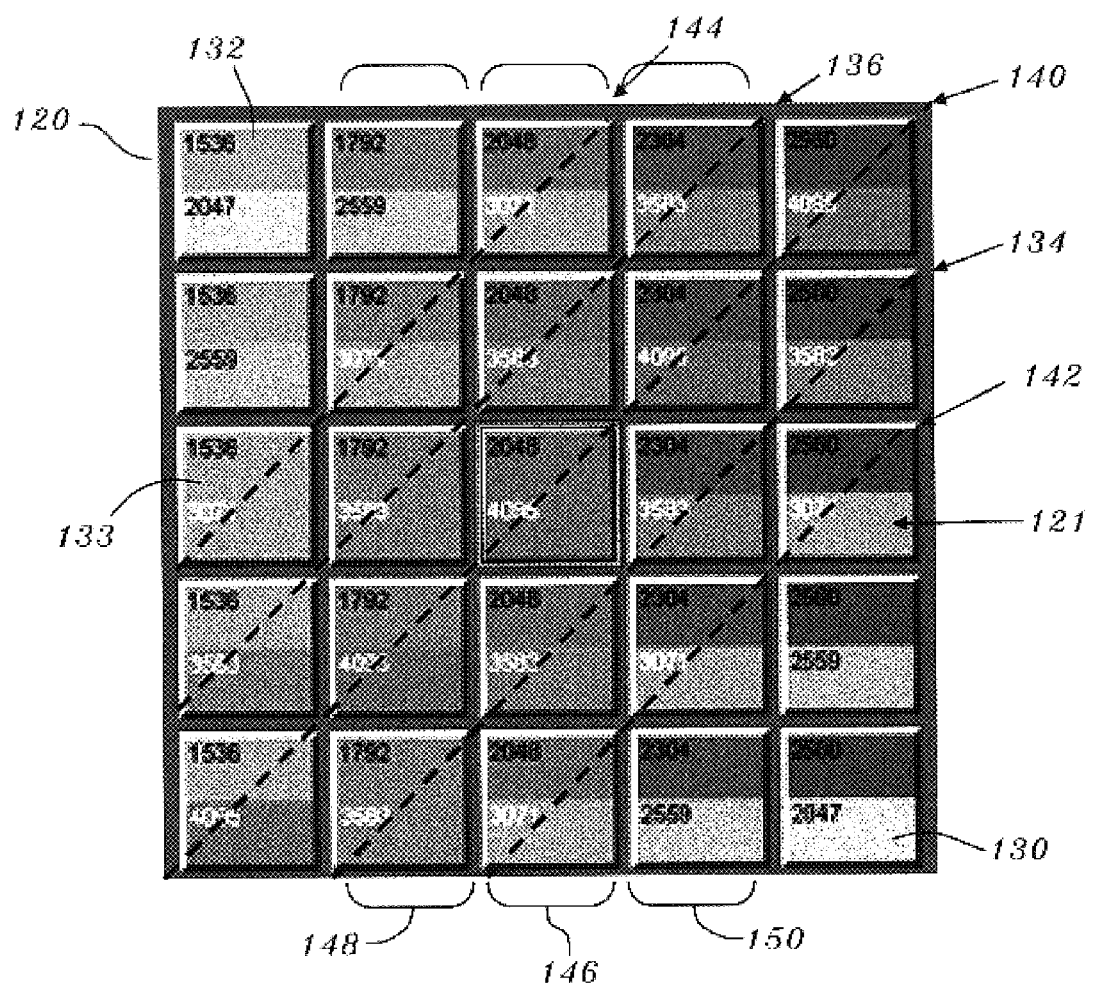
FIG. 2A is a representation of the user interface of the invention.

FIG. 2A shows user interface 120 in more detail. In the depicted embodiment, user interface 120 consists of a matrix of selectable icons 121. FIG. 2A shows user interface 120 as a 5×5 matrix. Larger or smaller matrices may be used. In addition, the selectable icons may be arranged in structures other than a matrix. Each of the selectable icon in the depicted matrix displays a visual cue indicating the effect achieved by the selection of the icon. In the embodiment depicted in FIG. 2A, the selectable icons display visual cues for window and level settings achieved by the selection of an icon.

Window and level are display setting terms used in the field of digital radiography. Window and level are sometimes interchangeably used with contrast and brightness. The window value of an image or display represents the width or range of grayscale pixels that are displayed, and the level value represents the center of the range. A low value for level will produce a brighter image, while a high value for level will produce a darker image. A large window value indicates that pixels will be displayed across a wide range of grayscale values, and as such, the image will have lower contrast. On the other hand, a small window value indicates that pixels will be displayed across a narrow range of grayscale values. This will produce an image with a high degree of contrast, as pixels with grayscale values that fall outside the window range will be mapped to either pure white or black.

Window and level values are important in digital radiography, as their adjustment allows a technologist or physician to view different types of body tissues. For example, tissues with different densities will often produce distinct grayscale levels in an X-ray image. Adjustment of window and level values allow a physician to focus on specific tissue types. In addition, the adjustment of window and level values may be used by a technologist to ensure that the digital radiographic image is of acceptable quality.

Figure 2B:
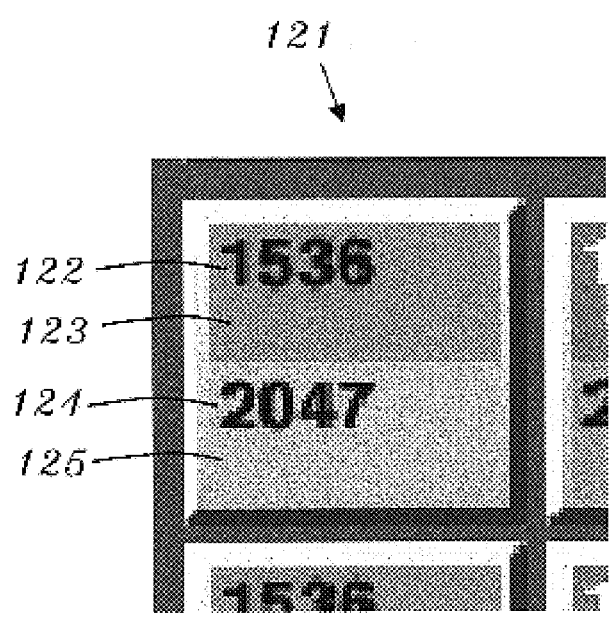
FIG. 2B is a representation of a selectable icon of the user interface of the invention.

Referring now to FIG. 2B, each selectable icon 121 contains several visual cues which indicate to a user the effect of selecting the icon. Level number 122 reflects the level value that is set by selection of the icon, while window number 124 reflects the window value that is set by selection of the icon. The level and window numbers displayed on each icon enable a user to quickly grasp the display setting achieved by selection of the icon. In order to further aid the user in making a selection, each selectable icon also includes a level grayscale patch 123 and a window grayscale patch 125. The level grayscale patch gives the user a visual cue as to the level (or brightness) achieved by selection of the icon. The window grayscale patch gives the user a visual cue as to the window setting (or contrast) achieved by selection of the icon.

Referring again to FIG. 2A, icon 130 in the lower right hand corner depicts a relatively dark level grayscale patch. As such, a user could expect that the selection of that icon would result in a fairly dark image. The window level grayscale patch for that icon is considerably lighter than the level grayscale patch. As such, the visual cue for that icon also indicates that the resulting image will have a high degree of contrast.

The arrangement of the icons within the user interface also provides a user with visual cues indicating in a relative manner how an image will change as different icons are selected. For example, icon 132 in the upper left-hand corner of the matrix has the same window value, 2047, as icon 130. However, icon 132 has a much lower level value. As icon 130 has the same window value as icon 132, both icons have the same grayscale patch for the window value. However, icon 130 has a much darker level grayscale patch than icon 132. This indicates to the user that an image can be made darker by increasing the level value.

Similarly, the grayscale patches on the icons provide the user with an indication as to how the window value will affect the displayed image. For example, icon 132 in the upper left-hand corner of the matrix has the same level value, 1536, as icon 133. However, icon 130 has a much lower window value. As icon 130 has the same level value as icon 133, both icons have the same grayscale patch for the level value. However, icon 133 has a window grayscale patch that is close in grayscale appearance to the level grayscale patch in icon 133. On the other hand, the window grayscale patch in icon 132 has a considerably different grayscale appearance in relation to the level grayscale patch in icon 132. This indicates to the user that an image can be made to have more contrast by decreasing the window value.

Figure 3:
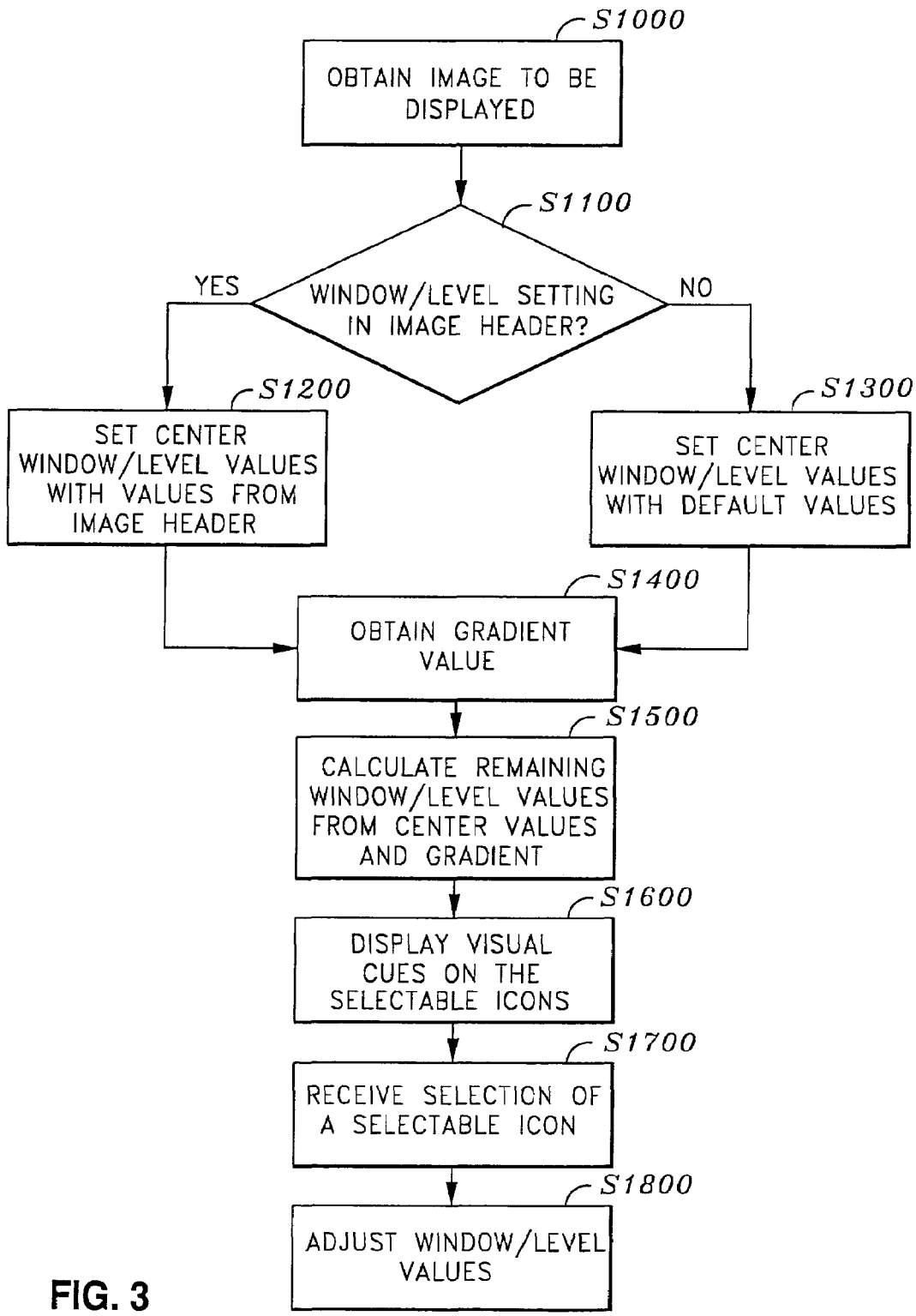
FIG. 3 is a flowchart depicting the use of the user interface of the invention.

FIG. 3 depicts a process for generating the visual cues for the selectable icons and for adjusting a display in response to the selection of an icon according to one embodiment of the invention. Initially, an digital image file to be displayed is obtained (S1000). The image may be a digital radiographic image, such as an X-ray, that is displayable by a computer program. Next, the header information in the image file is checked for window and level settings (S1100). In the case of medical images, the Digital Imaging and Communications in Medicine (DICOM) standard includes a field for window and level settings. If window and level settings are found in the header information, these settings are assigned as the center level value and center window value for the center selectable icon in the matrix (S1200). If no window and level settings are found in the header information, default center level and center window values are assigned to the center selectable icon in the matrix (S1300). As grayscale values typically range from 0 to 4095 in medical imaging applications, the default center window value may be set at 4095, and the default center level value may be set at 2048 (i.e. the middle of the maximum range). Other default values can be chosen as may be beneficial for particular image viewing situations.

Once the center window value and center level value are established, a gradient value is obtained (S1400). The gradient value is a percentage value which controls the degree of change in window and level values achieved by the selection of different icons across the matrix. The higher the gradient, the bigger the change in window and level settings will be achieved by the selection of different icons. The gradient value may be stored in a configuration file of a computer program or operating system utilizing the user interface of the invention. In addition, the gradient value may be input manually by a user.

Next, the remaining window and level values are calculated for each of the remaining icons (S1500). The window and level values are functions of the obtained center window and level values and the gradient. The window values are defined with relation to a center diagonal. As seen in FIG. 2A, the icons in the center diagonal going from the bottom-left to the top-right corner all have the window value of 4095. The window values for each of the other icons are calculated according to the following equation:

$$\text{WindowValue}(n) = \text{WindowCenter} - n * G * \text{WindowCenter} \quad (1)$$

wherein G represents the gradient, while n represents the number of steps in front or behind the center diagonal.

Referring again to FIG. 2A, user interface 120 shows icons with a window center value of 4095, and a gradient of 0.125. As such, the icons in diagonal 134 one step in front and a diagonal 136 one step behind a center diagonal 140 (each indicated by the diagonal dashed line) each have a window value of 3583. That is 4095−1*0.125*4095=3583. Likewise, icons in a diagonal 142 two steps in front and a diagonal 144 two steps behind the center diagonal each have a window value of 3071. That is 4095−2*0.125*4095=3071.

The level values are defined with relation to a center column. As seen in FIG. 2A, the icons in a center column 146 all have level values of 2048. The level values for each of the other icons are calculated according to the following equation.

$$\text{LevelValue}(m) = \text{LevelCenter} \pm m * G * \text{LevelCenter} \quad (2)$$

wherein G represents the gradient, while m represents the number of steps in front or behind the center column. In the case that a column being calculated is to the left of the center column, subtraction is used, and in the case that a column being calculated is to the right of the center column, addition is used. User interface 120 in FIG. 2A shows icons with a level center value of 2048, and a gradient of 0.125. As such, icons in a column 148 one step to the left of the center column have a level value of 1792. That is 2048−1*0.125*2048=1792. Likewise, the icons in a column 150 one step to the right of the center column have a level value of 2304. That is 2048+1*0.125*2048=2304.

Other equations and arrangements could be used for the calculation of the window and level values for the icons. For instance, rather than a linear equation, it may be beneficial to use a logarithmic equation for certain applications. In addition, as discussed above, varying gradients may be employed to achieve more or less varied window and level values.

Referring again to FIG. 3, after the window and level values for each of the icons have been calculated, visual cues are displayed on the selectable icons (S1600). The visual cues may include window numbers and level numbers, window grayscale patches and level grayscale patches, or a combination of both. The window number and level number used for each icon is identical to the window and level values calculated in S1500. Grayscale patches are generated in accordance with window and level values associated with each icon. The grayscale patches may be generated directly from the window and level values obtained and calculated in steps S1300 to S1500. In addition, the grayscale patches may be stored in lookup tables that correlate window, level and gradient values to the grayscale patches that are to be displayed on the icons.

Furthermore, the grayscale patches may be predetermined in accordance with the equation for determining window and level values, so that the grayscale patches reflect a relative window and level setting achieved by the selection of an icon. For instance, equation (2) shows that level values for the matrix of icons will be progressively greater from left to right in the matrix. As such, the level grayscale patches may be preset so that they show relatively light patches to relatively dark patches from left to right across the matrix. Likewise, in accordance with equation (1), the window grayscale patches may be preset so that high contrast is shown in the upper-left and lower-right corners, and relatively lesser degrees of contrast are shown as the buttons converge to the middle on a diagonal.

Next, a selection of one of the icons is received (S1700), such as through a mouse click. The computer program or operating system utilizing the user interface of the invention adjusts the display with the window and level values associated with the selected icon (S1800).

Figure 4:
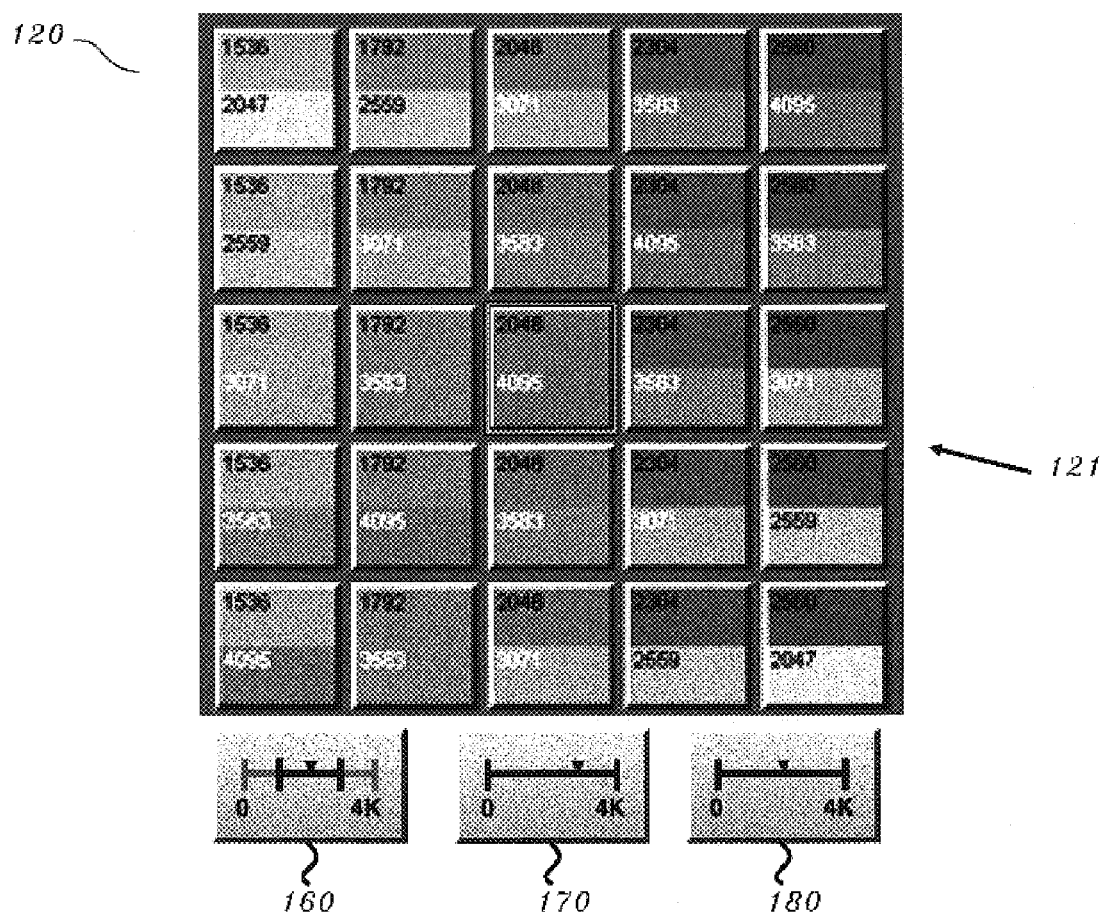
FIG. 4 is a representation of the user interface and reset icons of the invention.

FIG. 4 depicts another embodiment of the user interface of the invention. In this embodiment, user interface 120 further includes selectable window reset icon 160, selectable level reset icon 170, and selectable window/level reset icon 180. These reset icons allow for further control over the range of display parameters adjustable by the user interface.

Window reset icon 160 allows a user to control the range of window values achievable with the user interface. When the user selects the window reset icon, the currently selected window value is moved to the center window value, and the remaining window values are recalculated with the equation (1) described above. In addition, the window number and window grayscale patch visual cues are updated. As such, selection of the window reset icon causes a different range of window values to be displayed on the selectable icons, while the level values remain the same.

Likewise, selection of the level reset icon 170, causes a different range of level values to be displayed on the selectable icons, while the window values remain the same. When the user selects the level reset icon, the currently selected level value is moved to the center level value, and the remaining level values are recalculated with the equation (2) described above. In addition, the window number and window grayscale patch visual cues are updated.

The window reset icon and the level reset icon allow the user to adjust the user interface to allow for finer control of either window and level values about a specified value. In this way, finer control over the level and window values can be achieved without adjusting the gradient.

The window/level reset icon 180 is provided to enable the user to reset user interface back to the display parameters originally calculated for the image being displayed. Selection of this button, in effect, causes the process described with reference FIG. 3 to be repeated. In this way, a user can easily go back to the original settings for an image after selections of either the window reset or level reset icons.

Figure 5:
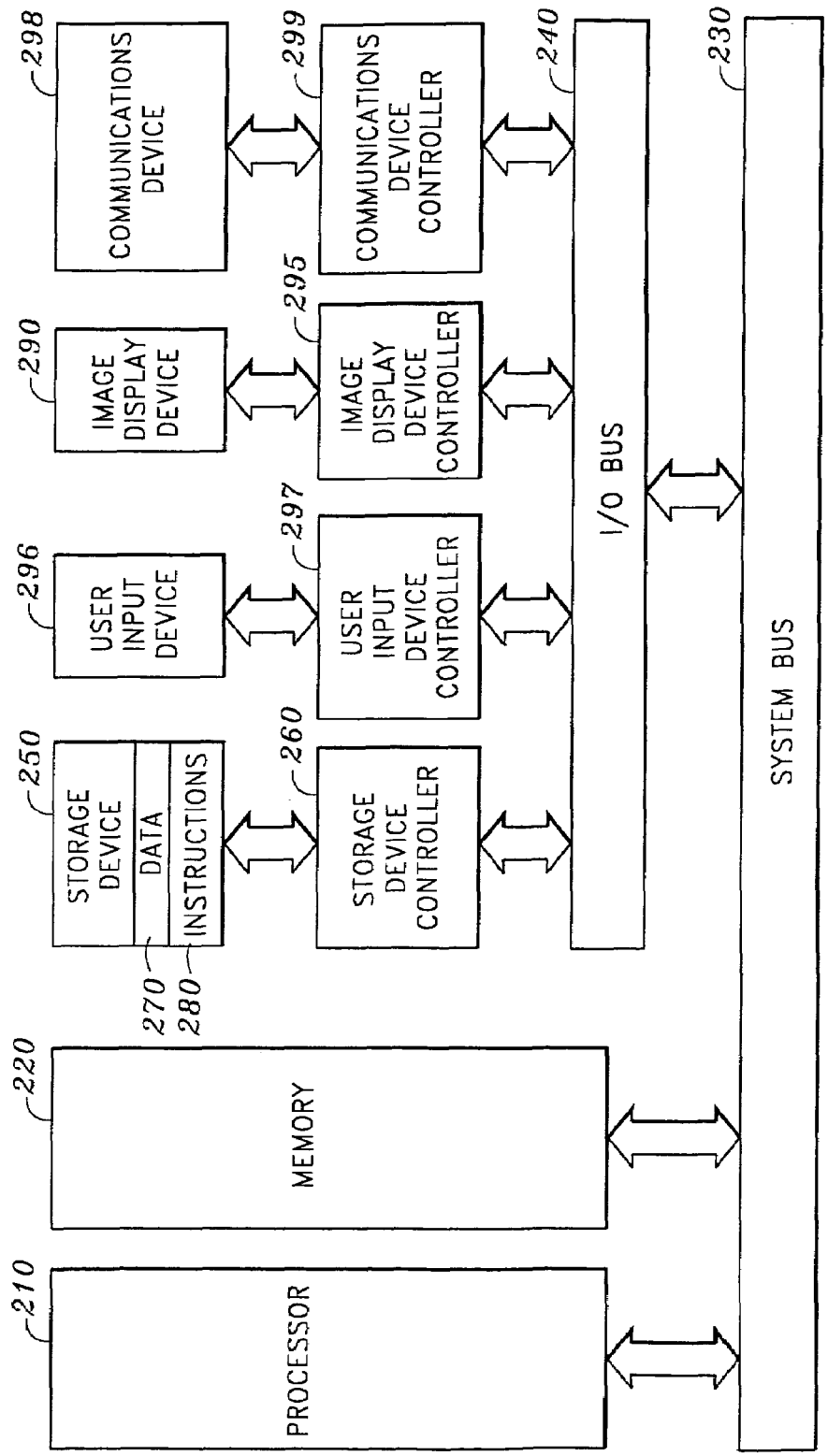
FIG. 5 is a block diagram of a data processing system that may be used to carry out the invention

FIG. 5 is a block diagram of a data processing system that may be used to carry out the invention described above. The data processing system 200 includes a processor 210 coupled to a memory 220 via system bus 230. The processor is also coupled to external Input/Output (I/O) devices via the system bus and an I/O bus 240. A storage device having computer system readable media 250 is coupled to the processor via a storage device controller 260 and the I/O bus and the system bus. The storage device is used by the processor to store and read data 270 and program instructions 280 used to implement the process for generating the visual cues for the selectable icons and for adjusting a display in response to the selection of an icon as described above.

The processor may be further coupled to a image display device 290 via a image display device controller 295 coupled to the I/O bus. The processor uses the image display device to display a user interface, including selectable icons and visual cues, as well as an image.

The processor may be further coupled to a user input device 296 via a user input device controller 297 coupled to the I/O bus. The processor uses the user input device to receive a selection of one of the icons.

The processor may be further coupled to a communications device 298 via a communications device controller 299 coupled to the I/O bus.

In operation, the processor loads the program instructions from the storage device into the memory. The processor executes the loaded program instructions to obtain an image to be displayed, set center window and level values, obtain a gradient, calculate window and level values for the icons, display visual cues on the icons, receive a selection of an icon, and adjust window and level settings of a display as described above.

The invention has been described above with respect to particular illustrative embodiments. It is understood that the invention is not limited to the above-described embodiments and that various changes and modifications may be made by those skilled in the relevant art without departing from the spirit and scope of the invention.

What is claimed is:

1. A display adjustment apparatus for adjusting image display parameters of a display of a radiographic image, comprising:
    a display device controller coupled to a processor by an I/O bus, for controlling a display of a plurality of selectable icons, each icon including a first visual cue area which includes a grayscale patch representing a value of a level setting, and a second visual cue area which includes a grayscale patch representing a value of a window setting, wherein the first visual cue area is separate from the second visual cue area within each icon;
    an input unit that receives a selection operation, which is a single selection of one of the plurality of icons; and
    a display processing unit that adjusts the display of the radiographic image by applying the first and second values associated with the selected icon to the display, in response to the selection operation,
    wherein the display device controller controls to display the plurality of selectable icons such that the plurality of selectable icons are arranged in a matrix, wherein selectable icons with equivalent level values are arranged along columns of the matrix, and wherein selectable icons with equivalent window values are arranged along diagonals of the matrix.

2. The display adjustment apparatus according to claim 1, wherein the visual cue areas further include a level number indicating the level setting and a window number indicating the window setting.

3. The display adjustment apparatus according to claim 1, further comprising:
    a calculation unit for calculating the level setting and the window setting for each of the selectable icons, and for generating the level grayscale patch and window grayscale patch for each of the selectable icons.

4. The display adjustment apparatus according to claim 3, wherein the arrangement of the window grayscale patches and level grayscale patches provides an additional visual cue as to how window and level settings are affected by selections across the matrix.

5. The display adjustment apparatus according to claim 3, wherein the calculation unit calculates the level setting and window setting using a function of a center level value, a center window value, and a gradient.

6. The display adjustment apparatus according to claim 5, wherein the center level value and the center window value are obtained from a digital image file to be displayed.

7. The display adjustment apparatus according to claim 6, further comprising:
    a selectable level reset icon;
    a selectable window reset icon;
    a selectable window/level reset icon;
    a level recalculation unit for recalculating the level setting for each of the selectable icons in response to a selection of the level reset icon, wherein a currently selected level setting is assigned as the center level value, and the remaining level settings are recalculated using a function of the assigned center level value and the gradient;
    a window recalculation unit for recalculating the window setting for each of the selectable icons in response to a selection of the window reset icon, wherein a currently selected window setting is assigned as the center window value, and the remaining window settings are recalculated using a function of the assigned center window value and the gradient; and
    a window/level reset unit for resetting the window setting and level setting to default values in response to a selection of the window/level reset icon.

8. The display adjustment apparatus according to claim 1, further comprising a memory, wherein the display processing unit executes instructions stored in the memory to adjust the display of the radiographic image.

9. The display adjustment apparatus according to claim 1, wherein said display processing unit comprises a processor.

10. The display adjustment apparatus according to claim 1, further comprising a display for displaying the radiographic image.

11. A display adjustment method for adjusting image display parameters of a display of a radiographic image, the method comprising the steps of:
    generating a plurality of selectable icons, each icon including a first visual cue area which includes a grayscale patch representing a value of a level setting, and a second visual cue area which includes a grayscale patch representing a value of a window setting, wherein the first visual cue area is separate from the second visual cue area within each icon;
    receiving a selection operation, which is a single selection of one of the plurality of icons; and adjusting the display of the radiographic image by applying the first and second values associated with the selected icon to the display, in response to the selection operation, wherein the plurality of selectable icons are arranged in a matrix, wherein selectable icons with equivalent level values are arranged along columns of the matrix, and wherein selectable icons with equivalent window values are arranged along diagonals of the matrix.

12. The display adjustment method according to claim 11, wherein the visual cue areas include a level number indicating the level setting and a window number indicating the window setting.

13. The display adjustment method according to claim 11, wherein the generating step generates the level setting and window setting using a function of a center level value, a center window value, and a gradient.

14. The display adjustment method according to claim 13, wherein the center level value and the center window value are obtained from a digital image file to be displayed.

15. The display adjustment method according to claim 13, further comprising the steps of:

recalculating the level setting for each of the selectable icons in response to a selection of a level reset icon, wherein a currently selected level setting is assigned as the center level value, and the remaining level settings are recalculated using a function of the assigned center level value and the gradient;

recalculating the window setting for each of the selectable icons in response to a selection of a window reset icon, wherein a currently selected window setting is assigned as the center window value, and the remaining window settings are recalculated using a function of the assigned center window value and the gradient; and resetting the window setting and level setting to default values in response to a selection of a window/level reset icon.

16. Computer-executable process steps stored on a computer readable medium, said computer-executable process steps for adjusting image display parameters of a display, said computer-executable process steps comprising process steps executable to perform a method according to any of claims 11, 12 or 13 to 15.

17. A computer-readable medium which stores computer-executable process steps, the computer-executable process steps for adjusting image display parameters of a display, said computer-executable process steps comprising process steps executable to perform a method according to any of claims 11, 12 or 13 to 15.

\* \* \* \* \*